United States Patent [19]
LeMay

[11] 4,289,968
[45] * Sep. 15, 1981

[54] RADIOGRAPHY

[75] Inventor: Christopher A. G. LeMay, Osterley, England

[73] Assignee: EMI Limited, Hayes, England

[ * ] Notice: The portion of the term of this patent subsequent to Jan. 31, 1995, has been disclaimed.

[21] Appl. No.: 814,631

[22] Filed: Jul. 11, 1977

Related U.S. Application Data

[63] Continuation of Ser. No. 543,338, Jan. 23, 1975.

[51] Int. Cl.³ .............................................. G01N 21/00
[52] U.S. Cl. .............................. 250/445 T; 250/363 S
[58] Field of Search .................. 250/445 T, 360, 363 S

[56] References Cited

U.S. PATENT DOCUMENTS

| | | | |
|---|---|---|---|
| 3,778,614 | 12/1973 | Hounsfield | 250/362 |
| 3,780,290 | 12/1973 | Hoffer | 250/363 S |
| 3,784,820 | 1/1974 | Miraldi | 250/362 |
| 3,808,440 | 4/1974 | Petit-Clerc | 250/363 S |
| 3,852,611 | 12/1974 | Cesar | 250/445 T |
| 3,934,142 | 1/1976 | Hounsfield | 250/445 T |
| 3,940,625 | 2/1976 | Hounsfield | 250/490 |
| 4,071,760 | 1/1978 | LeMay | 250/445 T |

*Primary Examiner*—Alfred E. Smith
*Assistant Examiner*—Thomas P. O'Hare
*Attorney, Agent, or Firm*—Cooper, Dunham, Clark, Griffin & Moran

[57] ABSTRACT

In an apparatus for examining a body by means of penetrating radiation a source is arranged to direct radiation through the body and a plurality of detectors are arranged to receive it thereafter. The source and detector are arranged to scan the body to obtain data for use in obtaining a distribution of absorption of the radiation for part of the body. For correction for differences in the relative sensitivities of the detectors they are arranged in pairs to examine radiation along substantially identical paths and for correction for drift each detector is caused to examine a substantially identical path at different times.

2 Claims, 9 Drawing Figures

RADIOGRAPHY

This is a continuation of application Ser. No. 543,338, filed Jan. 23, 1975.

This invention relates to a method of and apparatus for examining a body by means of radiation such as X- or γ- radiation.

The method and apparatus according to the invention can be used to assist in the production of radiographs in any convenient form, such as a picture on a cathode ray tube or other image forming device, a photograph of such a picture, or a map of absorption coefficients such as may be produced by a digital computer and on which contours may subsequently be drawn.

In the method of, and apparatus for, examining a body described in U.S. Pat. No. 3,778,614 radiation is directed through part of the body, from an external source, in the form of a pencil beam. A scanning movement is imposed on the beam so that it takes up in turn a large number of differing dispositions, and a detector is used to provide a measure of the adsorption of the beam in each such disposition after the beam has passed through the body. The beam is caused to take up these various dispositions by arranging that the source and the detector are reciprocated in a plane and are orbited about an axis normal to the plane. The various dispositions thus lie in a plane through the body over which the distribution of absorption coefficients for the radiation used is derived by processing the beam absorption data provided by the detector. The processing is such that the finally displayed distribution of absorption is the result of a linear superposition process coupled with successive approximations.

The method and apparatus described in the aforesaid Patent has proved to be successful for producing cross-sectional representations of parts of the living body, such as the head.

In the U.S. Ser. No. 532,188 now U.S. Pat. No. 3,999,073 filed Dec. 12, 1974 (Hounsfield et al) there is described an apparatus for carrying out the derivation of the absorption data signals in a relatively rapid manner. According to this Patent Application the derivation is achieved by directing a sectoral swath of X-rays emanating from a source, through the body in the plane to be examined and providing a series of detectors on the other side of the body to measure the radiation transmitted along a set of beam paths within the swath. The sectoral swath subtends an angle sufficient to include the whole region of interest in the plane of the body, so that a complete scan can be effected merely by orbiting the source and the detectors about the body. When such an arrangement is adopted it is important that the absorption data signals should not include differences due to differential variations in the sensitivites of the various detectors. It is, however, found in practice that such differential variations can occur to a significant degree even in the relatively short time required for scanning.

It is an object of the present invention to provide means for reducing such spurious differences.

According to one aspect of the present invention there is provided an apparatus for examining a body by means of penetrating radiation such as X- or γ- radiation including source means arranged to irradiate a region of the body, detector means, including a plurality of detectors, arranged to determine the intensity of the radiation after passage through the body, scanning means arranged to scan said source and detector means to irradiate the body from a plurality of directions so that there can be derived, from said determinations of intensity, a reconstruction of the distribution of absorption of the radiation within a part of the body, means being provided to compare the outputs of said detectors in pairs at predetermined times when the respective detectors of a pair receives radiation along substantially identical paths to determine the differences in the relative sensitivities of said detectors during the scanning movement.

According to a further aspect of the present invention there is provided a method of examining a body by means of penetrating radiation such as X- or γ- radiation including the steps irradiating a region of the body, detecting the intensity of the radiation, after passage through the body, moving the source of the radiation and a plurality of detectors with respect to the body so as to irradiate the body from a plurality of directions, deriving from said intensity determinations of reconstruction of the distribution of absorption of the radiation within a part of the body and comparing the outputs of said detectors in pairs at predetermined times in the course of the scanning movement to determine the extent of differences in the sensitivites of the detectors.

In order that the invention may be clearly understood and readily carried into effect, the same will now be more fully described with reference to the accompanying drawings in which.

Figure 1:
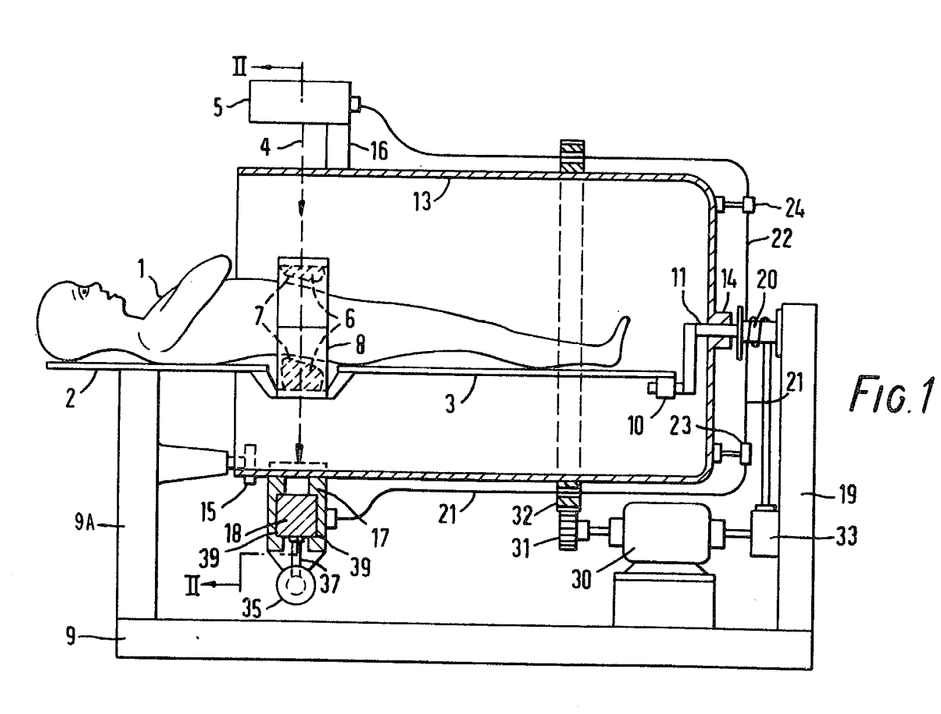
FIG. 1 shows the general layout in side elevation of an apparatus in accordance with the invention.

In FIG. 1 the patient 1 is shown lying on supporting means formed in two parts 2 and 3 and his body is subject to examination by X-radiation indicated in broken line at 4. This radiation is generated by a source 5 and forms a fan shaped spread in a plane lying at right angles to the plane of the figure. It will be appreciated that the patient supporting means has to be sufficiently long to allow any desired section of the patient's body to be located in the plane of the X-radiation.

In the region of the exploring radiation, the body of the patient is surrounded by a liquid medium, which may be water and which has an absorption coefficient for the radiation closely similar to that of body tissue. The liquid is shown in the figure at 6 and contained within an envelope, or bag 7. The envelope 7 is positioned within a ring like structure 8 which may be of metal such as duralumin. The ring member 8 is held by retaining means not shown in the figure. Supporting means 2 is mounted on an upright 9A of the main frame 9 of the apparatus whilst the part 3 is supported at its end remote from the ring member 8 by a bearing 10, carried by an axle member 11, which member has an axis about which orbiting motion of the X-ray source 5 takes place. Around the body of the patient, when he is located in position in the apparatus, there is disposed a surround or frame 13 which is cylindrical along its length, having a longitudinal axis which is the axis of the axle member 11. At its end adjacent this latter member, it is closed and supported by a bearing 14 which in turn is supported by the member 11. At its other end it is open to allow for positioning of the patient within it, and at this end it is supported on rollers 15 which have suitable fixed bearings. These rollers are such that the surround member 13 is free to rotate on its axis which, as has been indicated, is the axis about which the orbiting motion of the X-ray source 5 takes place. The source 5 is carried on the surround member 13 by means of a support 16. Directly opposite the source 5 there is carried on the surround member 13, by means of a support 17, a detector system 18 so as to provide radiation absorption data from the body of the patient in the plane of the radiation from the source 5. The detector system 18 extends over the whole spread of the fan of radiation from source 5. The spread of the fan is indicated diagrammatically in FIG. 2 as is the extent of the detector means 18. The supports for the detector system 18 allow limited angular movement of the system relative to the surround member 13, as will be described.

The axle member 11 is carried by a support 19 and adjacent the support 19 and surrounding the axle member 11 is a bobbin 20. This last element is fixed to the support 19 and wound round it are cables 21 and 22 respectively carrying absorption data from the detector means 18 to the processing unit and supplying power for the X-ray source 5. The cables 21 and 22 also supply electric current for electromagnets used for producing the aforesaid angular movements of the detector system 18. With the orbiting motion of the source and detector means the cables wind on or off the bobbin 20. They are fed to the bobbin via guides 23 and 24 respectively which are carried by the surround member 13. In this example of the invention, member 13 makes three revolutions for each examination cycle which is completed in a few seconds and the cables wrap or unwrap in relation to the bobbin 20 correspondingly, they are returned at the end of the examination. At the bobbin the cables are secured and thence pass to their respective connecting units, namely the data processing unit mentioned, and a power supply unit.

Figure 2:
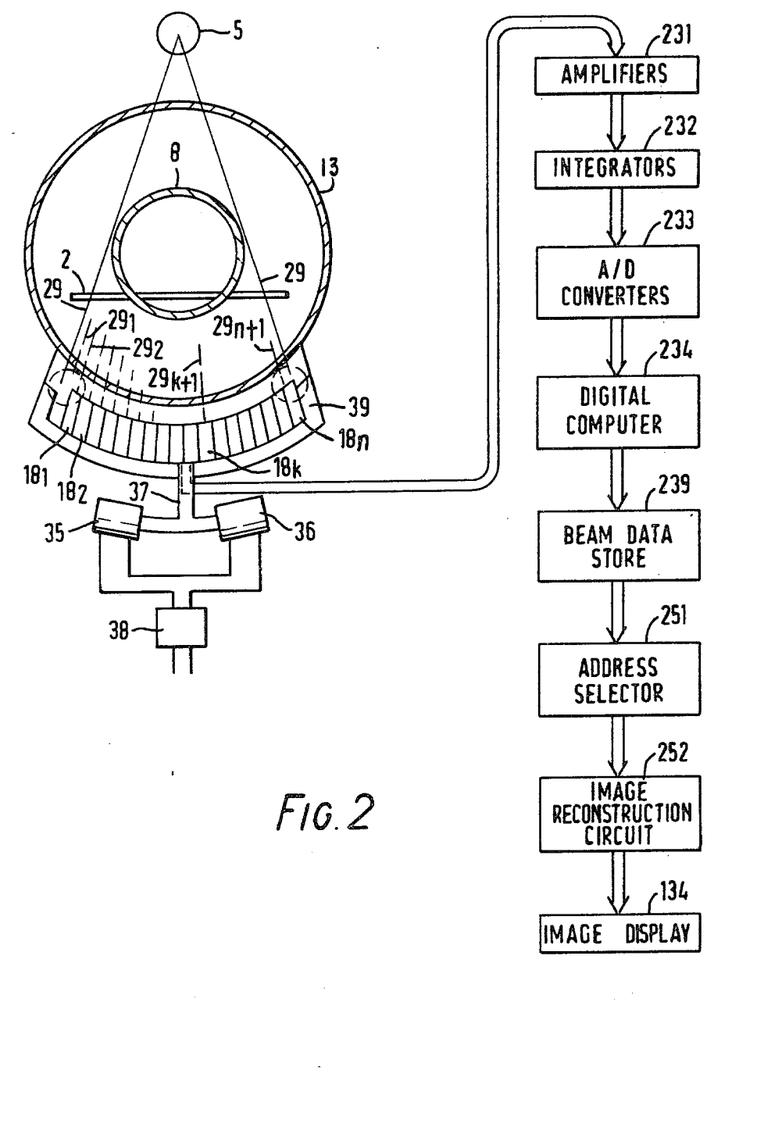
FIG. 2 shows details of part of FIG. 1, together with a diagrammatic layout of the circuit concerned with processing of the absorption data.

As indicated in FIG. 2, the detector means comprises a series of individual detectors $18_1 \ldots 18_k \ldots 18_n$, each arranged to detect the radiation transmitted along a narrow finger-like beam path $29_1 \ldots 29_{n+1}$, indicated in the sectoral swath which is limited within the bounds 29 by suitably collimating the sources of radiation 5.

Each detector $18_1 \ldots 8_n$ comprises in known manner a crystal which scintilates when a quantum of X-radiation or other high energy is incident upon it, and a photomultiplier for converting the light scintillation to an electrical current impulse, such impulses forming the output signals of the individual detectors. Other forms of detector may however be used. Each scintillator is provided with a suitable collimator so that radiation is substantially prevented from reaching it other than from the respective beam path. The construction of the apparatus shown in FIG. 1 is only illustrated in outline and briefly described, since it may be generally similar in construction to that described in the U.S. Ser. No. 532,188 filed Dec. 12, 1974 (Hounsfield et al).

The orbiting movement of the surround member 13 and with it the source 5 and the detector system 18 is effected by an electric motor 30, mounted on the main frame 9 which drives the surround member 13 via gear wheels 31 and 32, the latter of which is fixed to the surround member 13. The motor also drives a switching mechanism 33 which operates as will be explained on the current supply for the electromagnets which produces the angular movements of the source 5 and the detector system 18. The switching mechanism 33 also controls other supplies. FIG. 2 illustrates the electromagnet arrangement for the detector system. It comprises two coils 35 and 36 which operate an armature 37 attached to the detector system 18. The coils are connected in series with circuit supplied to a reversing switch 38 included in the switch mechanism 33. As shown, the detector system 18, which is a unitary structure is supported in guides 39 and attached to the surround member 13, the guide allowing a limited, but precise angular movement of the system 18. When the current supplied to the coils 35 and 36 has one sense, the system 18 is held in one of its limit positions on the guides 39, and when the current is reversed the system 18 is moved to the other limit position and held in that position. The switch mechanism 33 is arranged to operate the switch 38 after the first and again after the second of the three rotations of the surround member 13 which comprise the examination cycle of the apparatus. The movement of the detector system is very small, being only the angular separation between adjacent detectors $18_1 \ldots 18_n$.

The effect of the operation of the reversing switch 18 is to cause the detector $18_1 \ldots 18_n$ to detect the radiation received along the beam path $29_2 \ldots 29_{n+1}$ during the first and third revolution of an examination cycle and to detect radiation received along the beam paths $29_1 \ldots 29_n$ during the second revolution of the examination cycle.

Referring further to FIG. 2 the output signals from the detector system 18 as they are produced in the course of the orbital motion of the apparatus are fed to respective amplifiers 231. The various output currents from the amplifiers are respectively integrated by Miller integrator circuits 232, over successive short intervals of time and the outputs of these circuits are respectively converted from analogue to digital form by converters 233 and fed to the digital computer 234, the operation of which maybe explained in connection with FIG. 4. If desired the gains of the amplifiers 231 may be commonly controlled to compensate for any variations that may occur in the emission intensity of the X-ray source.

The outputs of the digital computer are corrected beam data signals, each one representing the transmittance of radiation along one of the beam paths $29_1 \ldots 29_k \ldots 29_n$ during an interval of time which is sufficiently short for it to be regarded as the transmittance along the stationary beam path at a particular angular position, notwithstanding the orbiting movement of the source 5 and the detector means 18. The beam path data signals are applied to beam data store 239 and thence via an address selector 251 to image reconstruction circuit 252 which may in fact utilise the digital computer 234. The image reconstruction will not be described here. It may be carried out in a variety of different ways but that described in the complete specification of U.S. Pat. No. 3,924,129 is preferred. It is sufficient for the purposes of the present invention to indicate that the address selector 251 withdraws data from storage in 239 in sets corresponding to output signals derived from parallel sets of beam paths, each set being processed in the circuit 252. It will be apparent from FIG. 2, that at any particular point in time (that is at any particular angular position of the sectoral swath 29) the beam paths $29_1 \ldots 29_k \ldots$ are not parallel. However, the intervals of integration of the integrators 232 are so related to the orbiting movement of the source 5 and the detectors 18 that beam path data signals, derived from successive detectors $18_1 \ldots 18_n$, during successive intervals of integration, represents the transmittance along parallel sets of beam paths. From a knowledge of the order of storage in store 239, sets of output signals corresponding to sets of parallel beam paths can be selected without difficulty. This mode of operation forms the subject matter of the U.S. Ser. No. 544,799 filed Jan. 28, 1975 now U.S. Pat. No. 4,206,389 (Hounsfield) and based on a British patent application filed on the day of filing of the British application on which this U.S. specification is based. When the image reconstruction operations are complete, the image is displayed by a display system 134, for example a cathode ray tube or printer, or in addition or as an alternative, may be transferred to magnetic tape storage.

The gains of the amplifiers 231 are adjusted to compensate for differences in the sensitivites of the radiation detectors. This compensation is particularly important when high accuracy in image reconstruction is aimed at, for example accuracy such as one part in one thousand. Sensitivity differences tend to appear in the reconstruction as a fine ring-like pattern. However, it is found in practice that pre-set adjustment in amplifier gains is insufficient to compensate for differences in sensitivities. The invention is concerned with effective compensation for differences which may exist or arise during each actual examination.

Figure 3A:
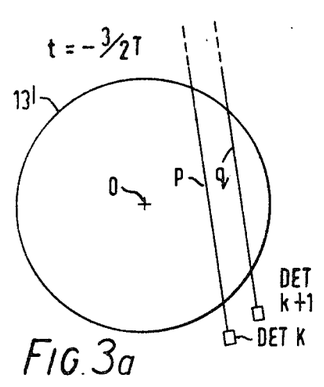
FIGS. 3(a), 3(b), 3(c), 3(d), 3(e) and 3(f) are explanatory diagrams relating to means according to the invention whereby data is corrected for detector errors.

It is possible to regard errors in the sensitivities of the detectors 18 as having two components, one dependent on the position of the detector (that is a difference in the sensitivity of the detector from a neighbouring detector) and the other dependent upon time (that is drift on the sensitivity of any one detector during the time occupied by an examination cycle). FIGS. 3(a) to 3(f) illustrate how these two components of error can be calculated approximately for each detector and used to correct the output data signals used in the image reconstruction. In each figure the area within which the body under examination must be located is shown by 13'. The figures indicate the beam paths along which radiation impinges on two detectors $18_k$ and $18_{k+1}$ at different times during the three revolutions of an examination cycle. FIG. 3(d) represents approximately the mid point of the second revolution at a time when, by virtue of the displacement of the detector system 18 affected by the electromagnets 35 and 36, the detectors k and k+1 are displaced, compared with their position at other times. The displacement is equivalent to displacing the orbital axis from 0 to 0'. One revolution is regarded as comprising 361, namely 0° to 360° inclusive, 1° of orbital movement occurring in each interval of integration of the integrators 232. The interval may however be smaller. The time occupied in each revolution of orbital motion is denoted by T and for mathematical convenience the time represented by FIG. 3(d) is taken as time t=o. The times represented by the other FIGS. 3(a), 3(b), 3(c), and 3(f) are indicated alongside the respective figures. The absorption data derived during the first and third revolutions is used for image reconstruction following techniques already described.

In each part of FIG. 3, it is assumed that the source of the exploring radiation, although not shown, lies in the plane of the figure vertically above the orbital axis O. In FIG. 3(a) the path p denotes a particular radiation track through the material of the body, radiation from the source traversing this track falling upon the kth detector $18k$ of the detector system 18. Detector k+1 is the next adjacent detector and radiation falling upon this detector traverses the path q through the material of the body. In FIG. 3(c) an identical situation is shown, with the completion of one revolution of the scanning, but now on account of drifting of the sensitivites of the detectors the absorption data derived from the two detectors may be different.

Figure 3B:
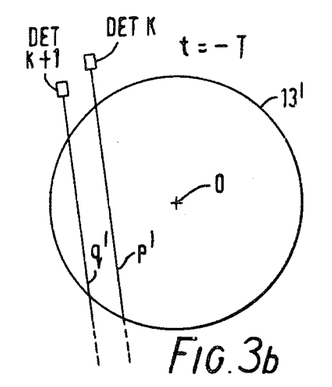

In FIG. 3(b) the positions of the two detectors are shown after just one half revolution of the orbital scan, and p' and q' designate radiation tracks through the material of the body that impinge upon the two detectors k and k+1 in the position they now occupy. The tracks lie in antisymmetrical relation to the tracks p and q.

The tracks p' and q' are also shown in FIG. 3(d) but now with the shift of the detector system it is radiation traversing track p' that falls upon detector k+1, rather than radiation traversing track q'. This interchange of the two detectors in relation to the path p' enables the sensitivities of the two detectors to be compared, and the manner of this comparison will become clear, though as will be evident it is necessary to take into account the extent of the drift of detector sensitivity in the interval between the time t=−T of FIG. 3(b) and the time t=o of FIG. 3(d). FIGS. 3(e) and 3(f) relate to the beginning and end of the third revolution of the examination cycle; these figures are similar to FIGS. 3(a) and 3(c) but the paths of the radiation incident on the detectors k and k+1 are denoted as r and s respectively to allow for the slight difference in the starting angle of the third revolution compared with the first revolution.

In order to understand the correction process in more detail let $S_k(t)$ represent the signal deriving from the kth detector at arbitary time t during the scanning operation. This signal will be proportional to the measure of absorption f(t) suffered by the exploring radiation along the path incident upon the detector at time t, and will also be proportional to the drift, $D_k(t)$, in the sensitivity of the detector at time t. Thus it is possible to write $$S_k(t) = A_k D_k(t) f(t).$$

A similar statement is true of the k+1th detector. $A_k$ may be termed the sensitivity constant of detector k. The output of detector k in FIG. 3(b) and that of detector k+1 in FIG. 3(d) are then $$S_k(-T) = A_k D_k(-T) f_0$$

$$S_{k+1}(0) = A_{k+1} D_{k+1}(0) f_0,$$

in which $f_0$ is the measure of the absorption along path p' in FIG. 3(b) and equally so along path p' in FIG. 3(d). To simplify matters the drift factor for a detector may be taken as unity for time t=0, and it follows then that $$\log S_{k+1}(O) - \log S_k(-T) = \log \frac{A_{k+1}}{A_k} - \log D_k(-T).$$

The ratio $$\frac{A_{k+1}}{A_k} = \lambda_k$$

can then be determined, and can furthermore be determined for any pair of detectors, if the magnitude of the drift as represented by $D_k(-T)$ can be determined. Therefore the relative sensitivities of the various detectors can be approximately compensated, providing that $\lambda$ and $D(t)$ can be determined in each case.

Figure 3C:
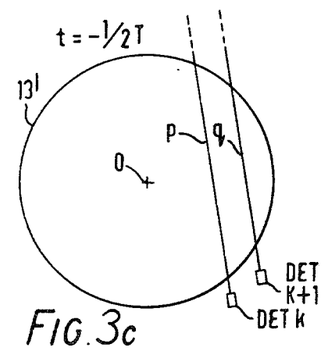
Figure 3D:
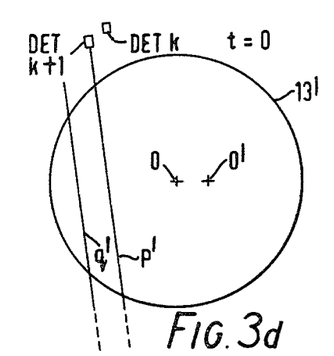
Figure 3E:
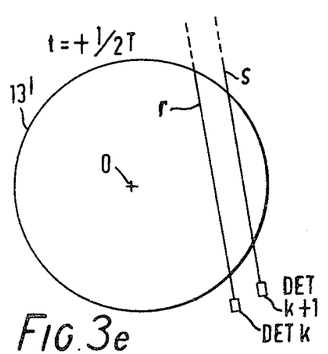
Figure 3F:
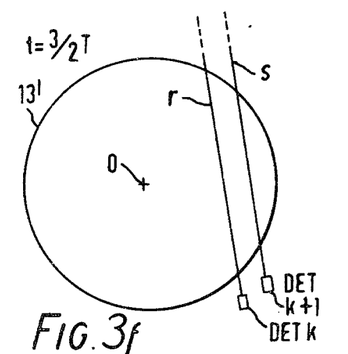

To obtain the information needed to evaluate $D(t)$, consider first of all the situations relating to FIGS. 3(a) and 3(c). For these situations respectively $$S_k\left(-\frac{3}{2}T\right) = A_k D_k\left(-\frac{3}{2}T\right) f_1$$

$$S_k(-\tfrac{1}{2}T) = A_k D_k(-\tfrac{1}{2}T) f_1,$$

in which $f_1$ is the absorption measure along the path p. Again considering the respective situations of FIGS. 3(e) and 3(f)

$$S_k(\tfrac{1}{2}T) = A_k D_k(\tfrac{1}{2}T) f_2$$

$$S_k\left(\frac{3}{2}T\right) = A_k D_k\left(\frac{3}{2}T\right) f_2,$$

of which $f_2$ is the absorption measure along the path p. From the first of the two pairs of equations it follows that $$\log S_k(-\tfrac{1}{2}T) - \log S_k\left(-\frac{3}{2}T\right) = \log D_k(-\tfrac{1}{2}T) - \log D_k\left(-\frac{3}{2}T\right),$$

and from the second $$\log S_k\left(\frac{3}{2}T\right) - \log S_k(\tfrac{1}{2}T) = \log D_k\left(\frac{3}{2}T\right) - \log D_k(\tfrac{1}{2}T).$$

These results may be represented more compactly if $\Delta_{k1}$ is used to signify the first order slope of a function associated with the k th detector over the span $(-(3/2)T)$, $(-\tfrac{1}{2}T)$, and $\Delta_{k2}$ likewise over the span $(\tfrac{1}{2}T, (3/2)T)$, so that the results can be expressed respectively, $$\Delta_{k1} \log S_K = \Delta_{k1} \log D_k$$

$$\Delta_{k2} \log S_k = \Delta_{k2} \log D_k.$$

On the assumption that the drift is small and that its logarithm can be regarded as varying in a parabolic manner, it is true to write $$\log D_k(t) = (\Delta_{k1} \log S_k + \Delta_{k2} \log S_k)t + \tfrac{1}{2}\Delta_{k12} \log S_k \cdot t^2,$$

in which $\Delta_{k12}$ signifies the second order slope derived from the first order slopes $\Delta_{k1}$ and $\Delta_{k2}$. Thus the drift $D_k(t)$ is determined for all times t during the examination cycle in terms of the four signal outputs $S_k(-3/2T)$, $S_k(-\tfrac{1}{2}T)$, $S_k(\tfrac{1}{2}T)$ and $S_k(3/2T)$. Every signal output of every detector can be corrected for drift, and knowing the drift in particular for time $t=-T$, the relative sensitivities of the various detectors may be allowed for as indicated earlier. Therefore the image reconstruction data can be compensated for the time variations occurring in detector sensitivity.

Figure 4:
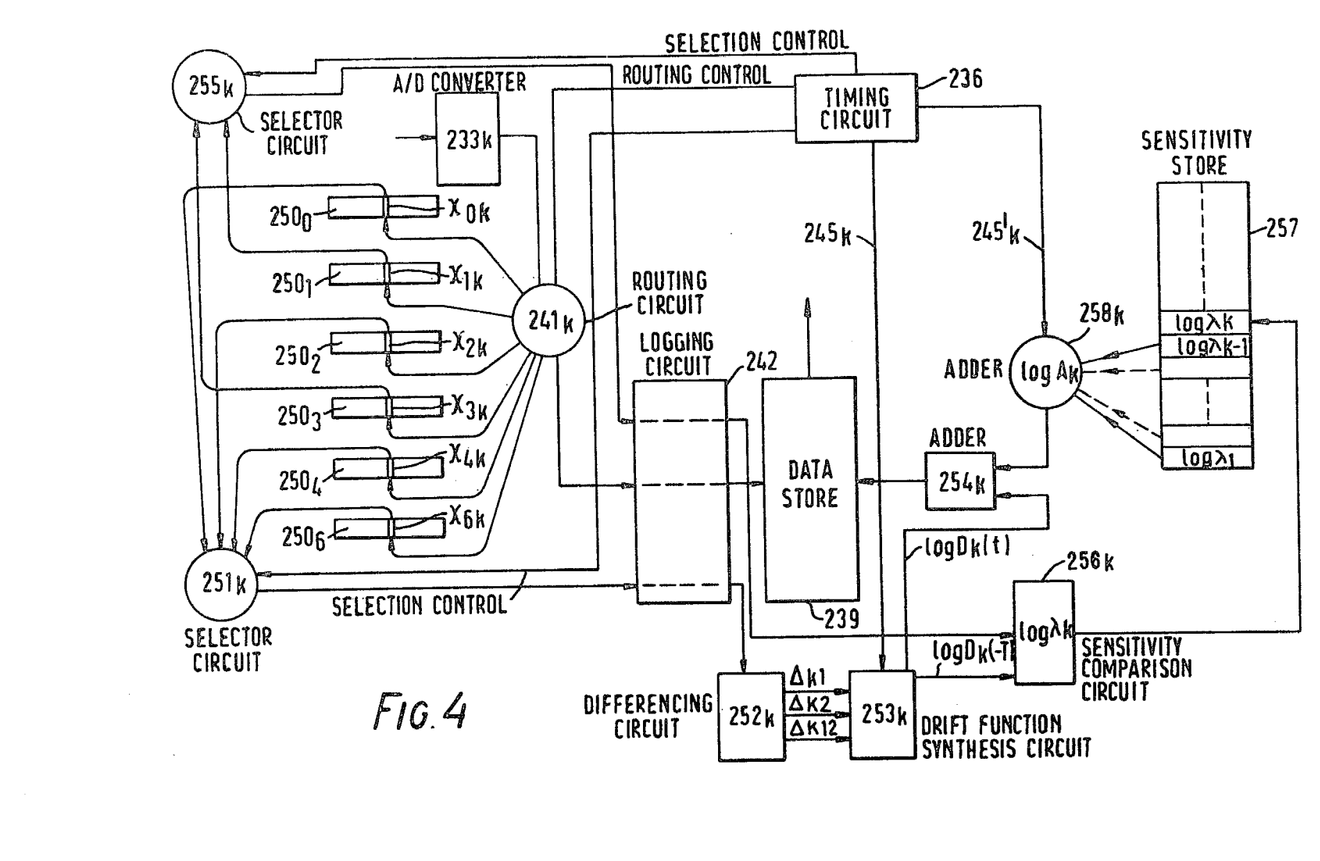
FIG. 4 is a diagram illustrating the operation carried out by a digital computer included in the circuit of FIG. 2.

Referring now to FIG. 4, the output signals from the integrator 232 (FIG. 2) are applied to analogue/digital converters 233 represented in FIG. 4 by a typical unit $233_k$. This receives the output from detector k which is then applied via a logging circuit 242, and other circuit elements to be explained hereinafter, to the data store 239, in which the beam data signals as initially stored require to be corrected for errors arising from detector sensitivity differences. from the store after correction the data is selected in desired order by address selector 251 (FIG. 2). The computer timing circuit or clock 236, a route selector circuit $241_k$ and the logging circuit 242 function in known manner under control of the computer programme.

To make the nature of the computer operations more clear, the relation between a corrected and uncorrected data signal held in the store 239 will be expressed as follows:

$$\log f(t) = \log S_k(t) - \log A_k - \log D_k(t).$$

In this expression f(t) is the true measure of absorption of radiation along the path through the body that is incident upon detector k at time t. The value in fact measured by the detector is $S_k(t)$. This value in its logarithmic form is initially stored in the data store 239 and correction is performed by subtracting from the uncorrected beam data signal the corrections $\log A_k$ and $\log D_k(t)$.

From what has earlier been said it will be realised that the correction of the data signals initially stored in store 239 requires detector output signals to be noted at times specified by:

$t = -3/2T,$ $t = -T,$ $t = -\tfrac{1}{2}T,$ $t = 0,$ $t = \tfrac{1}{2}T,$ $t = 3/2T.$ For simplicity the outputs of the kth detector at these times $-3/2T$, $-T$, $-\tfrac{1}{2}T$, $\tfrac{1}{2}T$ and $3/2T$ will be denoted in accordance with:

$S_k(-3/2T) = x_{0k}$ $S_k(-T) = x_{1k}$ $S_k(-\tfrac{1}{2}T) = x_{2k}$ $S_k(\tfrac{1}{2}T) = x_{4k}$ $S_k(3/2T) = x_{6k}$ and the output of detectors k+1 at time t=o will be denoted as $S_{k'}(o) = x_{3k'}$ These particular values, which appear in the output of the analogue-to-digital converter $233_k$, are routed by the route selecting circuit $241_k$, acting under the control of the timing circuit 236, to the kth address of respective stores $250_0$, $250_1$, $250_2$, $250_3$, $250_4$, $250_6$ as indicated. In these stores there is an address in each case corresponding to every detector channel, of which the kth is typical. It will be realised that the values in question except for $x_{3k'}$ also constitute image reconstruction data and are also stored in the data store 239. When the signals have been in stores $250_0$, $250_1$, $250_2$, $250_3$, $250_4$, $250_6$ a selector circuit $251_k$ withdraws the values $x_{0k'}$ $x_{2k}$, $x_{4k}$ and $x_{6k}$ in sequential manner, under control of the timing circuit 236, so as to feed them in sequence to the logging circuit 242. They emerge from the circuit 242 in logarithmic form and are applied to the differencing circuit $252_k$, which forms the first and second order slopes earlier introduced, and transfers these slope values to the drift function synthesis circuit $253_k$. This last circuit uses these values and values of the time parameter t to generate values of the logarithmic drift function log $D_k(t)$, in accordance with the assumption that this function varies parabolically with t as set out earlier. The values of t used in generating values of the function are those appropriate to the time of generation of the data signals fed to the store 239. Respective values of the function log $D_k(t)$ are applied to an adder circuit $254_k$ and thence subtractively to appropriate addresses in the data store 239. The appropriate values of t are communicated to the synthesis circuit $253_k$ over the conductor $245_k$. In this way the data signal held in store 239 originating from the detector k are corrected for all values of the parameter t used in image reconstruction. Following the same processing in similar circuit arrangements for all detector channels the entire data in store 239 is corrected for detector drift errors.

To follow the method of compensating the store data for position sensitive errors, that is unequal detector sensitivities it will first be noted that $$A_k = \frac{A_k}{A_{k-1}} \cdot \frac{A_{k-1}}{A_{k-2}} \cdots \cdots A_1,$$

in consequence of which, if $$\lambda_\nu = \frac{A_{\nu+1}}{A_\nu},$$

it follows that $$\log A_k = \sum_{1\nu}^{k-1} \log \lambda_\nu + \log A_1.$$

The compensation for unequal detector sensitivities involves the appropriate subtraction of the differing values of log $A_k$, differing for different values of k, from the data stored in store 239. Since the value log $A_1$ is common to all corrections, this value is disregarded on the ground that it would only introduce a uniform component into the image reconstruction. Thus where the value of log $A_k$ is referred to in future it will be understood to have the meaning $$\sum_{1\nu}^{k-1} \log \lambda_\nu.$$

From the discussion of the problem that has been given earlier it will be evident that the value of log $A_k$ is given by the equation $$\log x_{3k'} - \log x_{1k} = \log \lambda_k - \log D_k(-T),$$

in which, as stated earlier $$k' = k = 1.$$

The selector circuit $255_k$ under control by the timing circuit 236 selects in sequence the stored value $x_{3k'}$, stored in store $250_3$ and the stored value $x_{1k}$ from the store $250_1$ to apply them in turn to the logging circuit 242 and thence to a sensitivity comparison circuit $256_k$. This circuit uses the applied values together with the value of log $D_k(-T)$ generated by the drift function synthesis circuit $253_k$, and fed to the circuit $256_k$ under timing control by circuit 236, to synthesise the value of log $\lambda_k$ in accordance with the above equation giving log $\lambda_k$. The value of log $\lambda_k$ so synthesised is fed to the kth address of sensitivity store 257 which progressively receives and stores values of log $\lambda_k$ for all values of k. All values of log $\lambda_k$ are synthesised by respective circuits of the character just indicated.

To generate the value of log $A_K$ the adder circuit $258_k$ withdraws from store 257 all stored values of log $\lambda_\nu$ for values of $\nu$ given in the range 1, 2, 3, ... k−1, under the timing control of circuit 236 via conductor $245'_k$, and sums them so generating the required value of log $A_k$. This value is applied to the adder circuit $254_k$ and thence subtractively to the appropriate addresses in store 239. Using similar procedures to include all values of k the data stored at all addresses of data store 239 are compensated substantially for the unequal sensitivities of the detectors.

The components and circuits illustrated in FIG. 4 are merely shown diagrammatically because they are as already stated, implemented by a suitably programmed digital computer, which may be of any well known construction.

It will be understood that while detector values used in data signal correction as described are those of one detector position only, these values may be values averaged over a group of positions. In this way statistical errors from limited photon counts can be significantly reduced.

Furthermore, the detector values used in correction need not be obtained at the times indicated provided the timing of the circuit is arranged accordingly. Shorter scans and altered timings may be employed if desired to reduce the total time of scanning.

During the second revolution of the examination cycle, signals are derived from the detectors 18 only at time t=o. During the remainder of the revolution the X-rays may be cut off to reduce patient dose. Alternatively however, data signals may be generated during this second revolution and utilised in the image reconstruction.

It will be appreciated that the correction for time variable errors in detector sensitivity is achieved by deriving output signals from the respective detector at successive times when the radiation is incident on the detector, through the body being examined, along the same beam path. These output signals are utilised to generate a function representing the form of the drift in sensitivity, and discrete values of this function evaluated for respective instants of time are used to correct the respective output signals generated at the corresponding instants. Depending on the number of output signals used to generate the drift function, the function may be linear, parabolic, cubic or even higher order. In practice however parabolic function gives adequate correction. This aspect of the invention can be utilised with any number of detectors, since an individual drift function is generated for each detector. It is applicable where only one detector is used in each plane to be investigated, as described for example in U.S. Pat. No. 3,778,614.

The position sensitive correction is however based on receiving radiation along the same path by particular pairs of detectors (which need not in practice be constituted by adjacent detectors) in a detector system, one path for each pair. This aspect of the invention is therefore applicable only where multiple detectors are used. In the example described, the desired result is achieved by directing radiation twice through the body from substantially identical directions, and sensing the radiation emerging from the body at the first time with the detectors in one position relative to the body, and the second time with the detectors in a displaced position relative to the body. It will be understood however that the same effect could be achieved by displacing the body relative to the detectors, or by a combination of such movements. Moreover, the "look" through the body with the detectors displaced from their positions they occupy for normal scanning may take place either before and after the scanning movement, instead of as described, at an intermediate point. It is however preferable to check the relative sensitivities of the detectors at an intermediate point in the scanning process.

What I claim is:

1. Radiographic apparatus for examining at least one slice disposed cross-sectionally of a patient's body, comprising means defining a patient position including a region in which said at least one slice can be disposed, a source of a fan-shaped spread of penetrating radiation, support means supporting said source so that said radiation projects through said region along a plurality of beams which are distributed across said spread at respective angular orientations therein so that they diverge from one another with increasing distance from said source, means for moving said source angularly around the patient position to project said beams of radiation through said region from a plurality of locations distributed angularly around said patient position, detecting means, including a plurality of detector devices, disposed to detect said beams of radiation after they have traversed said region, and means causing relative movement between said spread of radiation and said detector devices whereby each beam of radiation is detected by a respective detector device at one stage of said angular movement of said source and by a different respective detector device at another stage of said angular movement.

2. Medical radiographic apparatus for examining a cross-sectional slice of the body of a patient, the apparatus including: means defining a patient position; a source of a fan-shaped distribution of penetrating radiation; a support means supporting said source so that the radiation is projected through the patient position along a plurality of beams disposed at respective angular orientations in said distribution, said beams diverging from one another with increasing distance from said source to a sufficient extent to provide beams at least tangential to a region capable of including said cross-sectional slice; means for moving said source angularly around the patient position to project said beams of radiation through said region from a plurality of locations distributed angularly around said patient position; detecting means, including a plurality of detector devices, disposed to receive the radiation travelling along said beams, after it has traversed said region and to provide output signals, indicative of the attenuation suffered by the radiation in travelling along said beams, said detector devices being closely adjacent so as to be capable of detecting radiation travelling along contiguous beams of radiation; means for causing a relative movement between said spread of radiation and said detectors and therefore between said beams and said detectors so that each beam of radiation is detected by a respective detector device at one stage of said angular movement of said source and by a different respective detector device at another stage of said angular movement; and processing means for operating on the output signals to provide a representation of the distribution of attentuation of the radiation with position in the cross-sectional slice.

* * * * *